United States Patent [19]

Walker et al.

[11] Patent Number: 4,936,862

[45] Date of Patent: * Jun. 26, 1990

[54] METHOD OF DESIGNING AND MANUFACTURING A HUMAN JOINT PROSTHESIS

[76] Inventors: Peter S. Walker, 10, The Covert, Northwood N.W. London, England; Frederick C. Ewald, 4 Black Oak Rd., Weston, Mass. 02193

[*] Notice: The portion of the term of this patent subsequent to Apr. 18, 2006 has been disclaimed.

[21] Appl. No.: 188,477

[22] Filed: Apr. 29, 1988

Related U.S. Application Data

[63] Continuation-in-part of Ser. No. 97,286, Sep. 11, 1987, Pat. No. 4,822,365, which is a continuation-in-part of Ser. No. 868,609, May 30, 1986, abandoned.

[51] Int. Cl.$^5$ .......................... A61F 2/36; A61F 2/30
[52] U.S. Cl. ........................................ 623/23; 623/18; 623/66; 364/468
[58] Field of Search ..................... 623/16, 20, 22, 23, 623/66, 18; 364/468, 474.25, 474.24

[56] References Cited

U.S. PATENT DOCUMENTS

| | | | |
|---|---|---|---|
| 4,663,720 | 5/1987 | Duret et al. | 364/474.25 |
| 4,742,464 | 5/1988 | Duret et al. | 364/474.25 |
| 4,769,040 | 9/1988 | Wevers | 623/20 |
| 4,778,475 | 10/1988 | Ranawat et al. | 623/23 |
| 4,822,365 | 4/1989 | Walker et al. | 623/66 X |

Primary Examiner—Alan W. Cannon
Attorney, Agent, or Firm—Wolf, Greenfield & Sacks

[57] ABSTRACT

A customized human joint prosthesis replicating the primary contours and dimensions of a patient's bone is designed and manufactured utilizing an average anatomical bone shape. The average anatomical bone shape is generated by digitizing and storing in a computer memory the average three dimensional shape of a significant number of actual bone portions corresponding to the bone portion to be replaced by the prosthesis. Thereafter, the scale of the patient's bone is determined by measuring the outside dimensions of the patient's bone in at least one plane parallel to the longitudinal axis of that bone. The average anatomical shape then is adjusted to form a first synthesized shape which conforms to that scale. Subsequently, the actual shape of the bone of the patient is measured along a plurality of longitudinally spaced lines in at least one plane normal to the longitudinal axis of the patient's bone. The first synthesized shape is then adjusted to form a second synthesized shape conforming to the measured shape of the patient's bone. The second synthesized shape is manufactured by CAD/CAM or other suitable means.

10 Claims, 6 Drawing Sheets

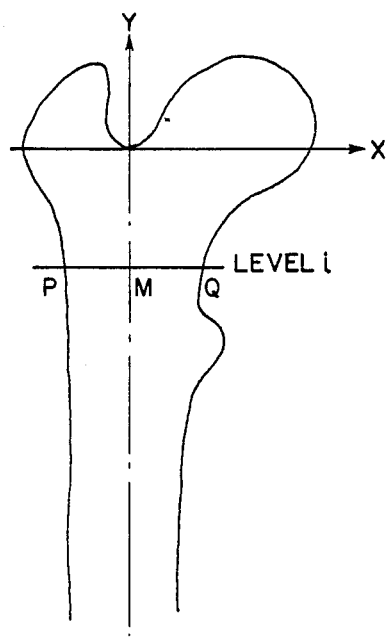
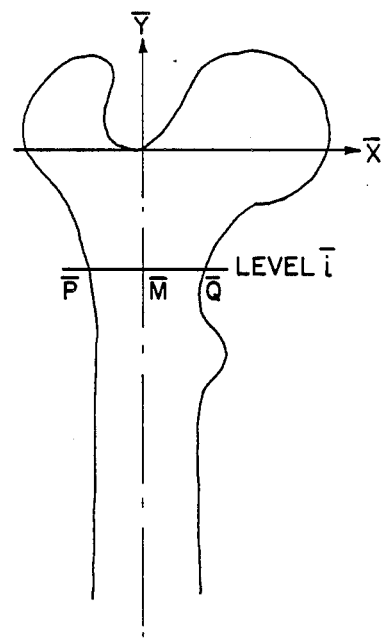
*Fig. 6A*  *Fig. 6B*
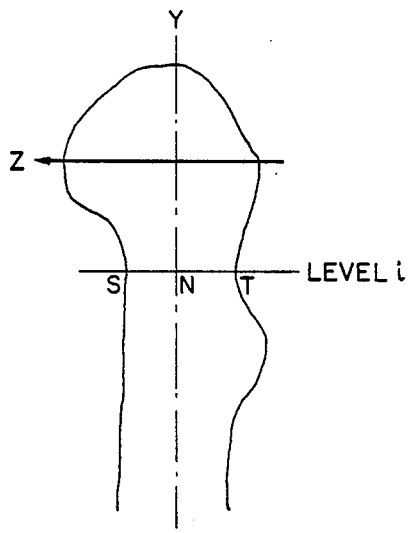
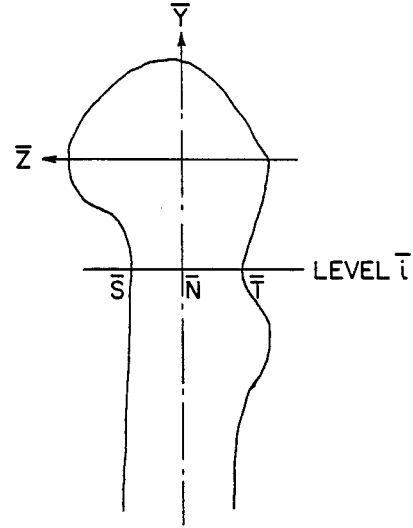
*Fig. 7A*  *Fig. 7B*

METHOD OF DESIGNING AND MANUFACTURING A HUMAN JOINT PROSTHESIS

This application is a continuation in part of our prior application Ser. No. 07/097,286, filed on Sept. 11, 1987, now U.S. Pat. No. 4,822,365 which was a continuation in part of our application Ser. No. 06/868,609, filed on May 30, 1986, now abandoned.

FIELD OF THE INVENTION

The present invention relates to a method of designing and manufacturing individualized prostheses for human joints. More particularly it relates to a method of generating prostheses by computer aided design and customizing prostheses to match specific bone shapes of individuals to produce a minimum of stress between the prosthesis and the supporting bone, and a maximum of stability therebetween.

BACKGROUND OF THE INVENTION

Recent efforts to improve the long-term fixation of femoral stems have focused primarily on press-fit designs often with some form of porous coating for biological ingrowth. Whether this approach will be successful and widely applicable is currently difficult to assess due to a number of issues. Firstly, the early results of contemporary cemented femoral components have improved since the introduction of modern cementing techniques (Cornell and Ranawat, 1986; Harris and McGann, 1986; Roberts, et al, 1986). Secondly, contemporary cementless prostheses may not be optimal in terms of design and in the use of the ingrowth materials, one consequence of which is inconsistency of bone ingrowth (Thomas, et al, 1987; Jasty, et al, 1987.) The early experience with a variety of cementless designs has led to some uncertainty about the relative importance of the many variables that must be tested in an effort to improve the clinical results.

A general conclusion that can be drawn from the previous work is that the clinical results improve with the degree of fit achieved at surgery, indicating that immediate stable fixation is of paramount importance to clinical success. (Ring, 1978; Engh, 1983; Ring, 1983; Itami, 1983; Morsher, 1983; Bombelli, 1984.) It has become clear, however, that certain design strategies for immediate fixation are inferior to others. For example, fixation achieved with long stems that are fully coated with an ingrowth material may produce deleterious proximal bone resorption (Brown and Ring, 1985). It is generally believed that if micromotion occurs between the stem and the bone during weightbearing, fibrous tissue will be formed (Cameron, et al, 1973) which can lead to eventual clinical loosening of the device. Primarily for this reason, the main thrust of the research in the United States has been to achieve primary biologic fixation with bone by the application of porous coating. To date, however, retrieval studies have reported that only a fraction of the acetabular and femoral surfaces achieve bone ingrowth.

Our initial approach to cementless stem design is based on the proposition that a stem shape that closely resembles the anatomy of the femoral canal, particularly in the proximal region, can achieve intimate contact and stability and approximate the load transmission patterns of the normal femur. The fit achieved with such an anatomic design, with the emphasis on maximum fit in certain priority, areas of contact, should result in maximal load transfer to cortical bone and resist not only axial and bending loads, but the important torsional loads as well.

A non-anatomic stem design can result in an apparently stable interface with a benign layer of fibrous tissue. (Kozinn, et al, 1986.) But, if the stem is much more inherently stable due to anatomic fit, and is constructed from an appropriate biocompatible material such as titanium alloy, it may be possible to achieve an interface of bone upgrowth with no interposition of fibrous tissue. (Lintner, et al, 1986; Linder, et al, 1983.)

The purpose of the present invention is to develop a method for the design and evaluation of a prosthesis including the combination of all of the significant elements on a given side of a human joint, for maximum geometric compatibility with the supporting bone structure of the recipient of the prosthesis. The object is to provide in such a prosthesis articulating surfaces and supporting elements therefore in combination to allow press-fit implantation and achieve sufficient stability to induce a stable biologic interface. A further purpose is to establish appropriate design parameters for initial stabilization, and thereby make it so that any ingrowth material at the interface of a joint which is made up of components so designed on both sides of the joint will thereby maximize formation of bone ingrowth and permit better evaluation in the future. An additional object of providing an anatomic design (including a relatively smooth articulating surface) is to increase versatility, whereby downsizing of the supporting elements can be performed to render them suitable for fixation with cement, and thereby to provide a uniform mantle with respect to cortical bone. A further object of the invention is to provide a substantially customized anatomical fit for prostheses for each patient, but to do it in a practically achievable and economical way.

BRIEF DESCRIPTION OF THE INVENTION

In the accomplishment of these and other objects of the invention in a preferred embodiment thereof a three dimensional model of an average joint bone including both the exterior surfaces and the cortical canal is developed using a statistically significant number of samples and by generating a piecewise mathematical analog thereof. The preferred method of calculating the surfaces and supporting elements comprises sectioning of embedded cadaver joints into a multiplicity of closely spaced segments (for example, 25 segments). (Alternatively, CT scan can be used to define the sections). The sections are then (copied and) digitized into a computer, using, for example, 30 to 40 points per section with a greater point density around regions of particular importance. Corresponding sections of equivalent levels of all of the bones are then averaged using a contour averaging routine. The digitalized representation of this average joint bone is then stored in the computer's memory. When it has been determined that an implant for a femur or other bone is required in a patient, the size and shape of the corresponding bone in the patient is determined by tomography or radiographs taken with the bone in fixed anterior-posterior, lateral-medial, and longitudinal axes. The relationships between the dimensions of the patient's bone on these axes and the stored average bone (scaled to correspond to the scale of the patient's bone) are then measured and input to the computer which then generates a three-dimensional shape which represents the average bone distorted to conform to the principal contours and dimensions of the patient's bone. The bone shape so generated, although derived from key linear dimensions of the patient's bone is essentially a synthesis of the average bone. The prosthesis shape, while replicating the predicted bone shape in certain areas, is relieved in other areas to enable it to be surgically insertable. The resulting computer generated shape is then fabricated using CAD/CAM and CNC techniques to provide prosthesis which closely approximates the patient's bone in the critical areas and thereby provides a maximum of stress free stability in the joint. It is a feature of the invention that the prosthesis, although it conforms accurately to the patient's bone in major ways and thereby provides a near optimum anatomical fit, is essentially derived from a synthesis of the stored average bone. Thus the process provides a virtually customized bone implant, but avoids the much more hazardous and costly task of attempting to determine the true shape (externally and internally) of the patient's bone by CAT scan and to duplicate it.

BRIEF DESCRIPTION OF THE DRAWINGS

An embodiment of the invention selected solely for purposes of illustration is shown in the accompanying drawings in which:

FIG. 6A is a view of a patient's bone taken along the anterior-posterior axis illustratively showing the location of two representative sections used in making the comparisons of the method of the invention;

FIG. 6B is a view of the average of a plurality of bones similar to the bone of FIG. 6A taken along the anterior-posterior axis illustratively showing the location of two representative sections used in making the comparisons of the method of the invention;

FIG. 7A is a view of a patient's bone taken along the lateral-medial axis illustratively showing the location of two representative sections used in making the comparisons of the method of the invention;

FIG. 7B is a view of the average of a plurality of bones similar to the bone of FIG. 7A taken along the lateral-medial axis illustratively showing the location of two representative sections used in making the comparisons of the method of the invention;

DETAILED DESCRIPTION OF THE INVENTION

The preferred embodiment of the present invention is described herein in connection with the design and manufacture of a prosthesis of a human femur, but it will be understood that the same process can be applied to any other joint, and either to both halves of the joint or simply to one half thereof.

The first step is to develop an average bone corresponding to the bone in question, in this instance, the femur. In the preferred embodiment herein described it was developed in the following manner:

The femurs of twenty-six human cadavers, aged in the 5th to 8th decades, were individually clamped in a jig to a reproducible axis system based on the center of the femoral head, and the straight part of the shaft just below the lesser trochanter. The center line of the shaft defined the vertical y-axis, the medial-lateral axis intersected the y-axis and the center of the femoral head, and the a-p axis was mutually perpendicular. A neck cut was made at 30 degrees from the horizontal, starting from the piriformis fossa. The cut surface was photographed to show the shape of the canal opening with respect to the orientation of the head and neck. The head was then reattached. The femurs were embedded and sectioned transversely, perpendicular to the y-axis. The section spacing was proportional to the length of the femur, measured from the top of the femoral head to the distal medial condyle. For a femur length of 500 mms, the proximal 21 sections were spaced at 5 mms, the distal 4 sections at 20 mms.

The sections were photographed and the cortical-cancellous interface of the femoral canal was identified for each section. Proximally, the inner and outer contours were virtually coincident due to the small cortical thickness. The inner and outer contours were then sequentially digitized into a computer.

Figure 1:
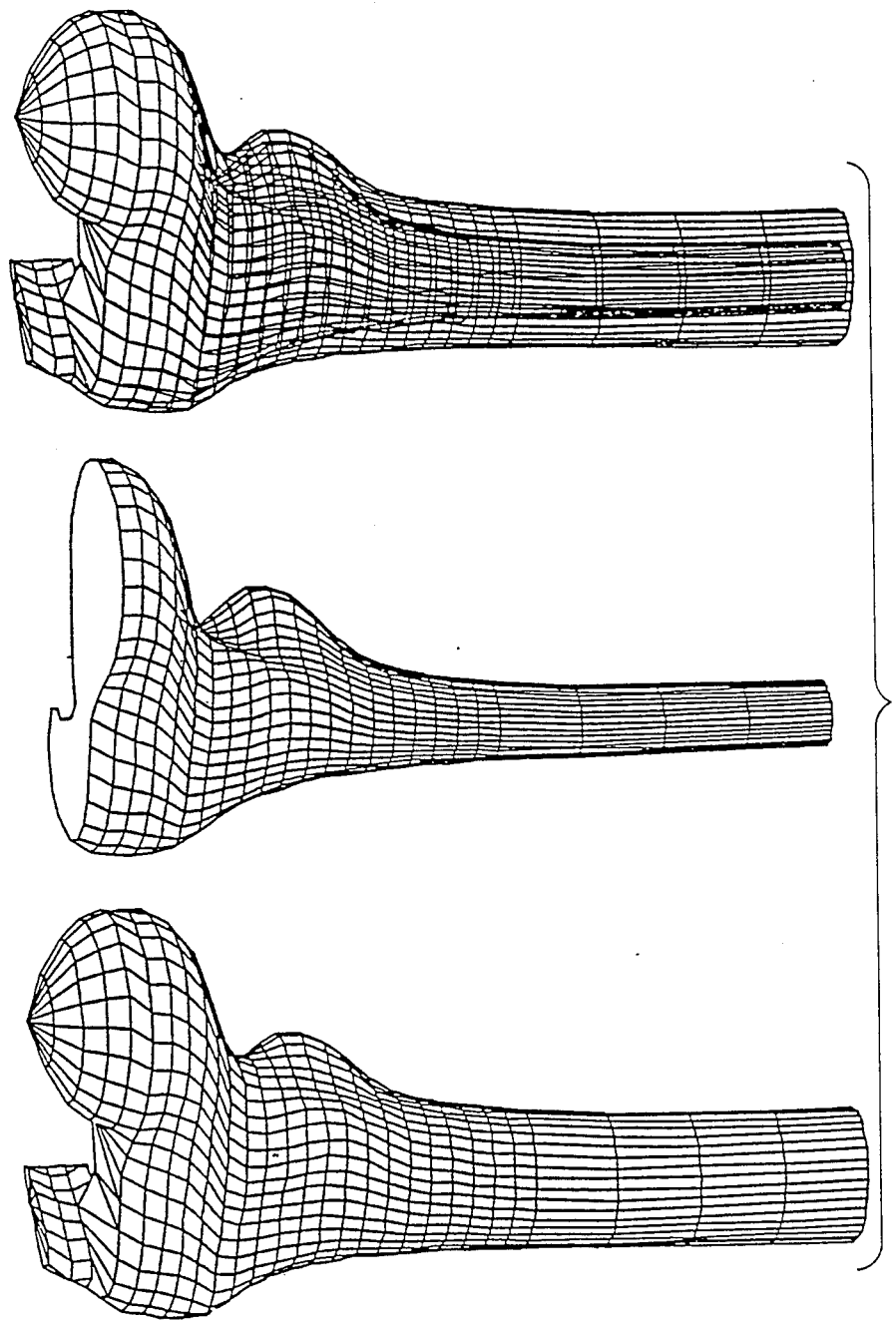
FIG. 1 is three-dimensional line view in perspective showing an average femur with outer surface to the left, the inner surface in the middle, and the outer and inner surfaces superimposed, to the right.

The boundary coordinates were scaled triaxially, according to equations derived from overall measurements of femurs from a skeleton bank (Terry Collection at the Smithsonian Museum). For each section, splining was used to determine the perimeter and then 40 uniformly spaced points were calculated with defined start- and mid-points. The section numbers were adjusted so that the level of the trochanteric fossa corresponded for all femurs. Compensation was next made for the location of the cente of the femoral head. This was done by using an alogorithm to stretch the coordinates to bring the center of the femoral heqad of each particular femur into the average location of the center of the femoral head. For the 26 bones, for each section, the coordinates of corresponding point numbers were then averaged. This produced an average femur which had a natural appearance and where each section was aligned smoothly to adjacent sections (FIG. 1, left hand view).

Next, the internal contour was determined. The goal here was to design an optimal-fit stem that maximized implant-bone fit while recognizing that the stem must be surgically insertable, but maintain fit in mechanically important regions. Three interactive software modules were developed to design a hip stem to fit the average 3-D bone model (Garg, et al, 1985; Nelson, 1985).

Figure 2:
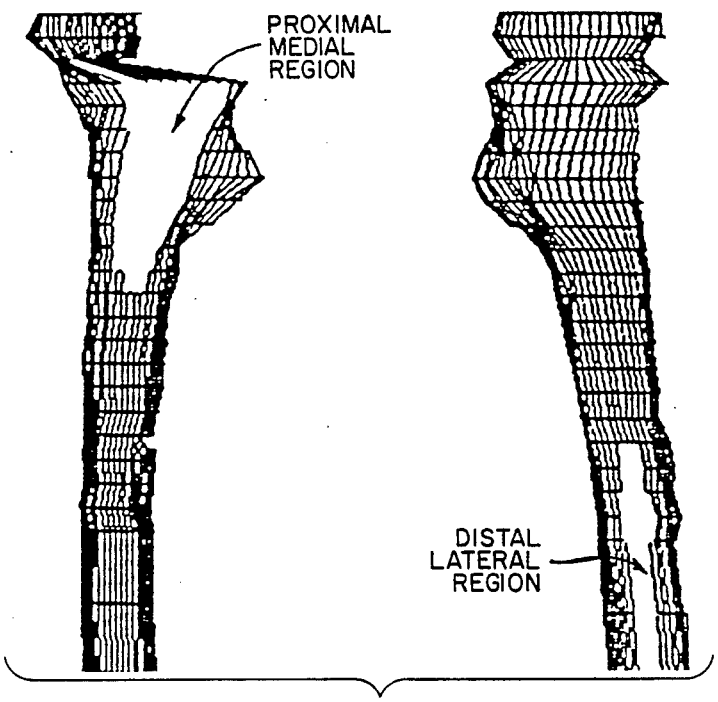
FIG. 2. is a three-dimensional line view in perspective showing the cortical canal, and the regions to which priority is assigned.

The first module simulated the surgical bone preparation to prepare the 3-D bone model for stem insertion. Interactive simulation of femoral head and neck resection and canal reaming and rasping were performed in this module. Inner cortical areas that were needed for efficient stem-bone load transfer and for minimizing stem motion were identified and assigned a priority score in this module. The particular high priority regions were the proximal-medial and distal-lateral walls (FIG. 2). Once this preparation was completed, the edited 3-D model was submitted to the second software module.

Figure 3:
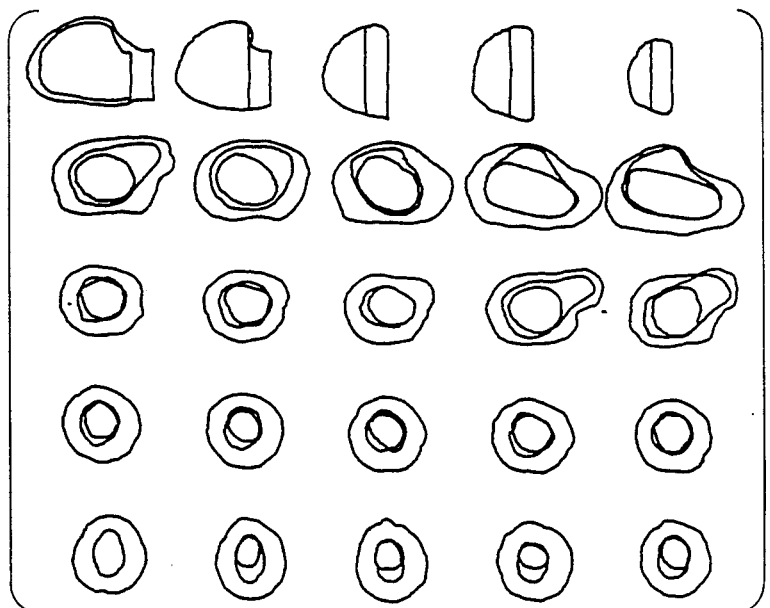
FIG. 3. shows cross-sectional cuts arranged sequentially, illustrating the optimal stem shape.
Figure 4:
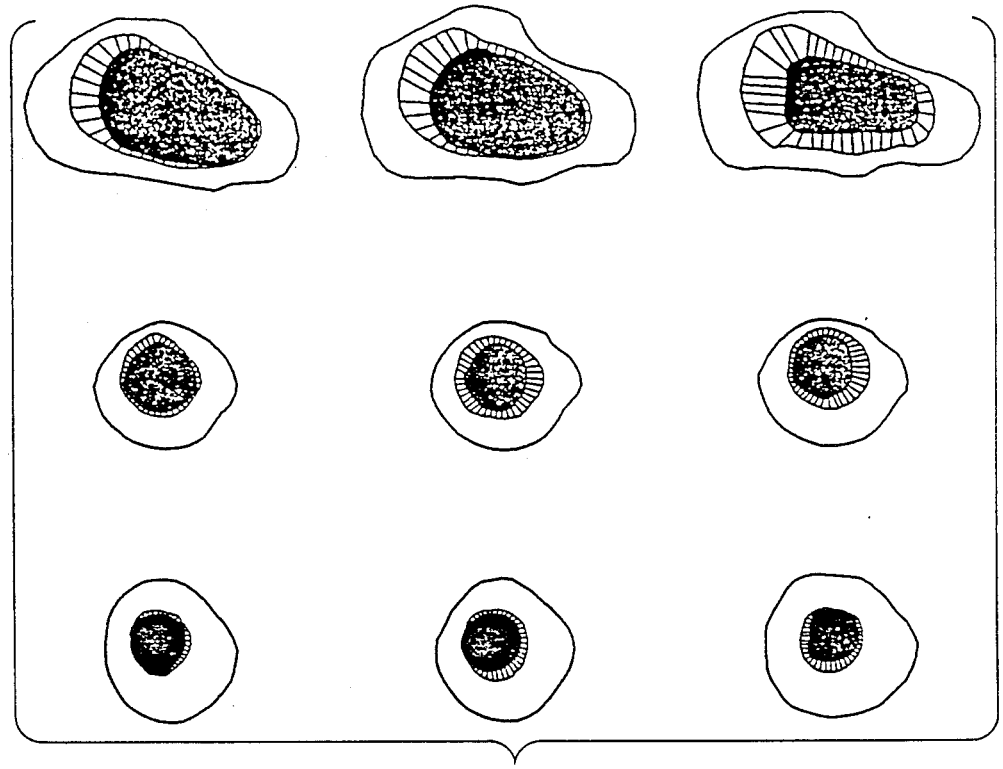
FIG. 4. shows the results of different stems fitted in bones for proximal, mid-stem, and distal regions, with the left hand representing individualized fit, the center optimal fit, and the right, a symmetric fit.
Figure 5:
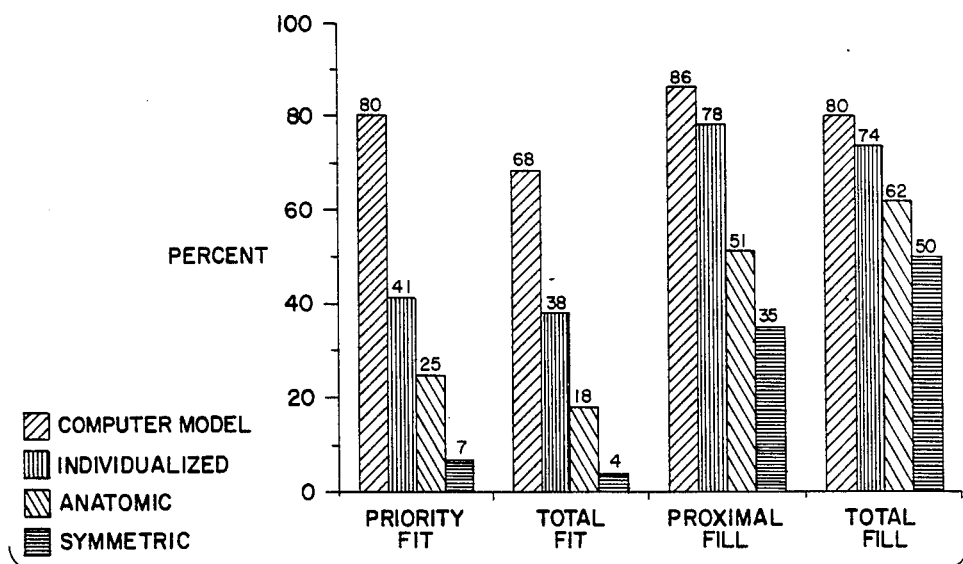
FIG. 5. is a bar graph comparing the percent of fit of prostheses made by 4 different methods.
Figure 8A:
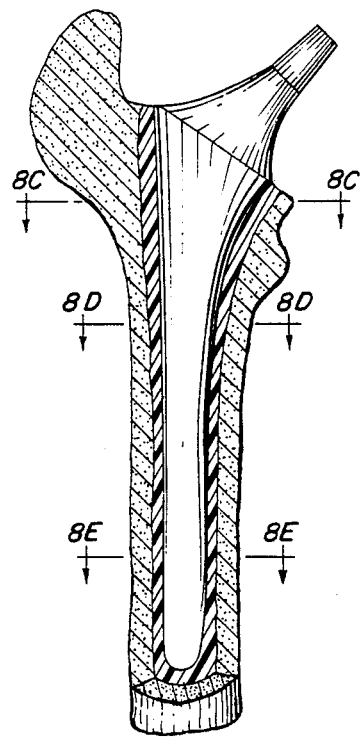
FIG. 8A is an X-ray derived view of the frontal section of an optimal-fit (profile) stem cemented into a bone showing a continuous cement mantle.
Figure 8B:
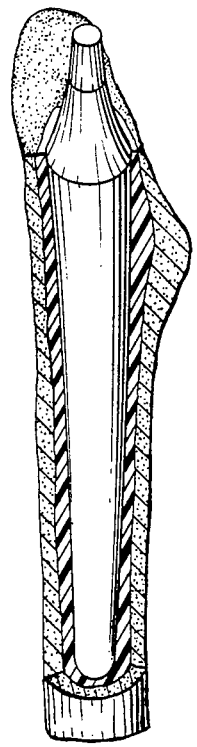
FIG. 8B is an X-ray derived view of the sagittal section of the bone and stem shown in FIG. 8A.
Figure 8C:
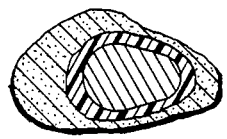
FIG. 8C is an X-ray derived view of a transverse section of the bone and stem shown in FIG. 8A taken along the line A—A.
Figure 8D:
FIG. 8D is an X-ray derived transverse section of the bone and stem of FIG. 8A taken along the line B—B.
Figure 8E:
FIG. 8E is an X-ray derived transverse section of the bone and stem of FIG. 8A taken along the line C—C.

The second module performed the actual stem design. The guiding principle was that, due to the three-dimensional curvature of the femoral canal, a stem that completely filled the canal could not be inserted. Thus, the stem had to be shaved down in certain regions. The design process began by setting the stem shape equal to the shape of the edited inner-cortical model. The stem was translated proximally an incremental amount along the vertical axis. Movements were then made in the other five degrees of freedom. At each given orientation, a stem-canal surface overlap score was determined, calculated as the point by point sum of the overlap distance multiplied by the priority value. Minimization of the overlap score was obtained by applying a modification of Newton's optimization algorithm. The stem was then moved to the orientation of minimal score and the overlapping stem regions removed by redefining them at their intersections with the bone canal. The stem was then elevated to the next level and the process repeated until the entire stem shape was withdrawn from the neck cut. The resultant stem shape described the optimal stem-canal fit which was still insertable (FIG. 3).

The third and final module was for verification and editing of the stem design. Computer graphics methods were used for qualitative assessment of implant-bone fit, while finite element analysis (FEA) was used to examine the mechanical environment of the implant and bone. Following these examinations, the computer-designed femoral stem could then be manufactured using CNC.

A standardized optimal-fit hip stem was thus designed for the average femoral geometry of the twenty six femurs described earlier. By using the average femur, it was assumed that the average misfit of the optimal stem would be minimized over a large number of femurs. As an interim measure, the stem was then scaled to produce six sizes and mirrored to produce rights and lefts.

Figure 9:
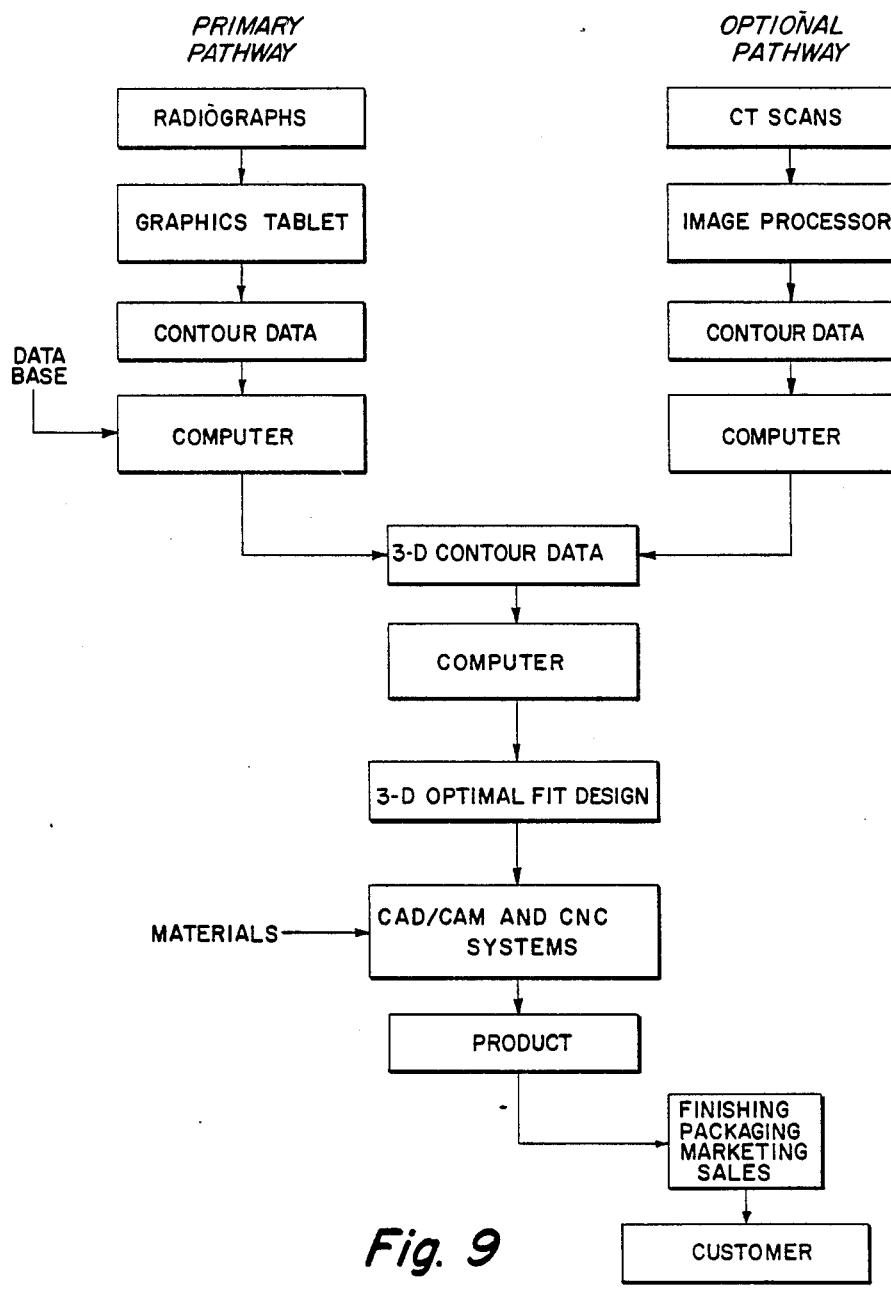
FIG. 9 is a flow chart setting forth the major steps of the process including alternative paths for input data concerning the patient's bone obtained from radiographs or from CT scans.

In the preferred process of this invention, the computerized average femur is stored and used thereafter to generate a prosthesis by the following steps:

By tomography or by the use of radiographs, the profiles of the patient's femur are determined on one of two views, such as the anterior-posterior and/or medial-lateral axes. To accomplish this, the patient's bone is positioned to align the plane subtended by the longitudinal axis of the femur and the median prominences of the greater and lesser trochanters normal to the axis of the camera. The resultant radiograph is placed on a graphics tablet (which can be a precision digitizer utilizing a microprocessor to calculate the cursor position from information detected by circuitry placed in the surface), and, using a mouse, the center axis (i.e., the Y axis) of the patient's femur is determined by establishing the coordinates of the outer contours of a plurality of points below the lesser trochanter. Once the center axis of the bone has been determined, a first scale-determining plane normal to the Y axis and passing through the lowermost extremity of the piriformis fossa is established, and then a second scale-determining plane is established normal to the Y axis of the femur and passing through the median prominence of the lesser trochanter. The axial dimension between these two scale-determining planes is used to adjust the scale of the average femur so that the upper scale-determining plane corresponds to the twenty-fifth section of the average femur, and the second scale-determining plane corresponds to the fifteenth section of the average femur. This scale-adjusted shape can be referred to as a "first synthesized shape". Then, having established the scale, the mouse is guided around the entire contour of the cortical canal and upper part of the femur. At each point of its passage, the coordinates are entered and compared to the corresponding points of the average femur and each section of the average femur is adjusted to conform around its entire periphery to the difference on this one axis between the patient's femur at that section and the average femur. This is done by placing the negative of the patient's femur on the graphics tablet and rapidly running the mouse around the patient's femur as represented by the radiograph. Once the scan has been completed, the computer determines the adjusted average femur which can be referred to as a "second synthesized shape". At this point a printout of it can be made, similar to FIG. 1, except that it will be adjusted to conform substantially to the femur of the patient, but with additional relief in certain areas of the stem to facilitate insertion. This can be regarded as the "3-D Optimal-fit Design" (see FIG. 9). The data thereof is then stored and used in the production of the implant by CAD/CAM and CNC techniques. The entire process from radiography of the patient's bone to production of the finished product can be performed in a few hours.

A special additional feature of the process is that the surgeon can improvise as he deems necessary in order to provide a joint which may be calculated, for example, to correct for previous deterioration of the patient's joint in order to restore the joint to correct dimensions which previously existed. In this case, the patient's bone is X-rayed and then the surgeon superimposes on the image the adjustments he deems necessary and the distortion of the average femur (i.e., the second synthesized shape) is based on the adjusted contour, rather than the actual radiograph.

In addition, the process permits an implant to be made, examined and further adjusted before actual implantation. Thus, if the surgeon, upon examining the radiographs together with an actual sample of the implant (or even before a first sample has been fabricated), detects that an insertion problem is presented, due to peculiarities of a given patient's cortical canal, he can rapidly have the sample adjusted, or a new sample fabricated. The process is, in fact, sufficiently rapid to have the equipment standing by to perform an adjustment during a surgical procedure.

It will be understood that the dimensions of the patient's bone can be radiographed on additional axes for fine tuning. In one embodiment, the patient's femur is radiographed additionally on the orthogonally disposed medial-lateral axis, and the same procedures of adjusting the average femur are carried out to include this further input. The resultant prosthesis is even closer to the patient's natural bone. Further "fine tuning" is not considered necessary.

Having thus described a preferred embodiment of our invention, it will be apparent to those skilled in the art that various modifications can be made without departing from its spirit. For example, while it is well-suited for designing and fabricating the femur, it can be used for other joints. In addition, additional levels longitudinally of the bone can be useful to detect differences in the angle of the cortical canal. Further, the stem portion of the prosthesis can be scaled down to permit the use of cement rather than a press-fit, while still benefitting from advantages of the invention. In addition, while we have described developing the average femur by sectioning the femurs of 26 humans, it will be understood that the important thing is to take a sufficient number of samples to establish an adequate bell curve to be statistically significant, and, thereby, produce a reliable average femur, or other bone, as the case may be. In addition, while tomography and radiography have been mentioned as the method of determining the contour of the patient's bone, other methods may be used. Accordingly, it is not intended to confine the invention to the precise form herein described, but to limit it only in terms of the appended claims.

We claim:

1. A method for making a prosthesis for a human joint bone comprising the steps of:
   a. determining the average anatomical three-dimensional shape of said bone by taking a sampling of a statistically significant number of actual bones, digitizing their three-dimensional shapes, correlating them proportionally as to overall size, and averaging them;
   b. storing said digitized average shape;
   c. determining the outside dimensions of the patient's corresponding bone on at least one plane parallel to the longitudinal axis of the bone;
   d. deriving a first synthesized shape by adjusting the scale of the stored average shape to conform to the scale of the patient's bone;
   e. determining the difference between the shape of the patient's bone and the first synthesized shape on a plurality of longitudinally-spaced lines in said at least one plane normal to the longitudinal axis of said bone;
   f. deriving a second synthesized shape by adjusting the first synthesized shape to conform its entire surface to the differences so determined at each respective line; and
   g. fabricating the prosthesis using the second synthesized shape.

2. The process defined in claim 1 further characterized by:
   determining the shape of the patient's bone on at least two planes parallel to the longitudinal axis of said bone, and
   determining the differences in the shape of the patient's bone and the first synthesized shape on corresponding lines in both said planes.

3. The process defined in claim 1 further characterized by:
   the shapes of both the average bone and the patient's bone including both the outer surfaces thereof, and the cortical canals.

4. The process defined in claim 1 further characterized by:
   adjusting the stored average shape to include relief to facilitate insertion.

5. The process defined in claim 1 further characterized by:
   adjusting the first synthesized shape to include additional predetermined distortions based on individual requirements of the patient.

6. The process defined in claim 1 further characterized by:
   adjusting the second synthesized shape to include additional predetermined distortions based on individual requirements of the patient.

7. The process defined in claim 1 further characterized by:
   the bone being the femur.

8. The process defined in claim 2 further characterized by:
   said two planes being orthogonally disposed.

9. The process defined in claim 7 further characterized by;
   the adjustment of scale being performed by establishing a first scale-defining plane normal to the axis of said bone passing through the piriformis fossa, and a second scale-defining plane passing through the median prominence of the lesser trochanter, and adjusting the scale of the average bone to conform thereto, at corresponding planes.

10. A method for making a prosthesis for a human joint bone comprising the steps of:
    a. determining the average anatomical three-dimensional shapes of both the outer contour and the cortical canal of said bone by taking a sampling of a statistically significant number of actual bones, digitizing their three-dimensional shapes, correlating them proportionally as to overall size, and averaging them;
    b. storing said digitized average shapes;
    c. determining the external and internal dimensions of the patient's corresponding bone by radiograph on at least two orthogonally disposed planes parallel to the longitudinal axis of the bone;
    d. deriving a first synthesized shape by adjusting the scale of the stored average shape to conform to the scale of the patient's bone;
    e. determining the difference between the shape of the patient's bone and the first synthesized shape at the intersections between the contours of said bone on the orthogonally disposed planes and plurality of longitudinally-spaced transverse planes normal to the longitudinal axis of said bone;
    f. deriving a second synthesized shape by adjusting the first synthesized shape to conform its entire surface to the differences so determined at each respective transverse plane; and
    g. fabricating the prosthesis using CAD/CAM based on the second synthesized shape.

* * * * *

UNITED STATES PATENT AND TRADEMARK OFFICE
CERTIFICATE OF CORRECTION

PATENT NO. : 4,936,862

DATED : June 26, 1990

INVENTOR(S) : Walker et al

It is certified that error appears in the above-identified patent and that said Letters Patent is hereby corrected as shown below:

Col. 7, line 33 - before "determining" insert -- a --.

Signed and Sealed this

Twenty-eighth Day of July, 1992

Attest:

DOUGLAS B. COMER

Attesting Officer

Acting Commissioner of Patents and Trademarks